United States Patent [19]

Masuda et al.

[11] Patent Number: 4,562,146
[45] Date of Patent: Dec. 31, 1985

[54] SILVER HALIDE COLOR PHOTOGRAPHIC MATERIAL

[75] Inventors: Kosaku Masuda, Akishima; Kaoru Miyagi, Tachikawa; Katsunori Katoh; Noritaka Nakayama, both of Hachioji; Toshihiko Kimura, Hino; Satoshi Kawakatsu, Hachioji, all of Japan

[73] Assignee: Konishiroku Photo Industry Co., Ltd., Tokyo, Japan

[21] Appl. No.: 672,143

[22] Filed: Nov. 16, 1984

[30] Foreign Application Priority Data

Nov. 18, 1983 [JP] Japan ............... 58-217339

[51] Int. Cl.[4] .................................. G03C 7/38
[52] U.S. Cl. .................................. 430/546; 430/551; 430/558
[58] Field of Search ............... 430/551, 549, 558, 546

[56] References Cited

U.S. PATENT DOCUMENTS 3,684,514 8/1972 Iwama et al. ............... 430/544
3,810,761 5/1974 Bailey et al. ............... 430/522

Primary Examiner—J. Travis Brown
Attorney, Agent, or Firm—Finnegan, Henderson, Farabow, Garrett & Dunner

[57] ABSTRACT

A silver halide color photographic material is disclosed. The material contains a photographic magenta coupler of formula (I) and a phenolic compound of formula (II) within a silver halide emulsion layer:

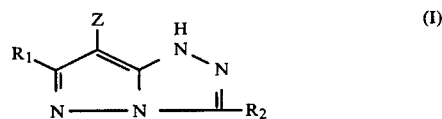

(I)

(wherein $R_1$ and $R_2$ are each an alkyl group or an aryl group; Z is a hydrogen atom or a group that can be eliminated upon coupling reaction with the oxidized product of a color developing agent);

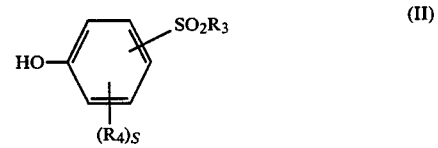

(II)

(wherein $R_3$ is an alkyl group, an alkoxy group, an aryl group or an amino group; $R_4$ is an alkyl group, an alkoxy group or a halogen atom; s is an integer of 0 to 2, provided that when s is 2, $R_4$ may be the same or different).

16 Claims, 1 Drawing Figure

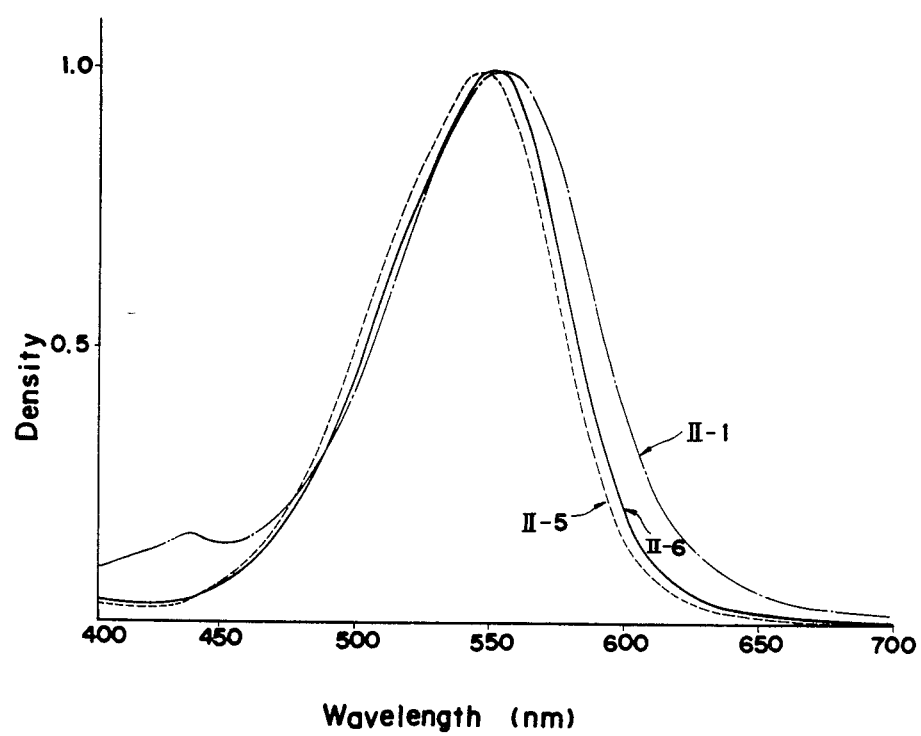

SILVER HALIDE COLOR PHOTOGRAPHIC MATERIAL

FIELD OF THE INVENTION

The present invention relates to a silver halide color photographic material which has high sensitivity and color density, exhibits good spectral absorption characteristics and provides a magenta dye image having improved keeping quality.

BACKGROUND OF THE INVENTION

In silver halide color photography, exposed silver halide grains are reduced with an aromatic primary amine color developing agent, and the resulting oxidized product of the developing agent enters into coupling with couplers which form yellow, magenta and cyan dyes.

Pyrazolone couplers are commonly used as the magenta dye forming coupler, but they have various problems. First, they have an undesired absorption in the wavelength range of 400–500 nm in addition to the desired predominant absorption by the magenta dye in the region of 540–560 nm. Secondly, the couplers have low maximum color density and sensitivity. Thirdly, these couplers do not have sufficient long-term stability and a raw photographic material that has been stored in the presence of formalin experiences a change in color shade and a reduction in color formability upon color development.

In order to solve these problems, many proposals have been made in the past. Japanese Patent Application (OPI) No. 42045/1983 (the symbol OPI as used herein means an unexamined published Japanese patent application) shows a coupler having good spectral absorption characteristics with a fairly long absorption wavelength at 552 nm. However, this coupler is not considered to be practical since it has low color sensitivity and density, as well as poor dispersion stability.

Japanese Patent Publication No. 16058/1974 shows a compound having good sensitivity and a fairly long absorption wavelength at 551 nm. However, this compound also has an undesired absorption in the range of 400 to 500 nm, and the color density of the compound is low.

U.S. Pat. No. 3,684,514 shows a compound that is high in both color sensitivity and color density. However, the absorption wavelength of the compound is as short as 543 nm, and the keeping quality of the compound in the presence of formalin is very poor.

Japanese Patent Application (OPI) No. 42045/1983 also shows using said coupler in combination with a certain phenolic compound. However, the absorption wavelength of the combination is still long (558 nm) and no significant improvement is achieved in color sensitivity.

European Pat. No. 74745 shows using a pyrazolone magenta coupler together with the phenolic compound defined in the present invention, but none of the advantages achieved by the present invention are suggested in this patent.

Active efforts have also been made to improve the performance of couplers by mixing with various additives. However, it is impossible to reduce the undesired absorption of pyrazolone magenta couplers by incorporation of other additives. It is therefore desired to improve the pyrazolotriazole magenta couplers shown in Japanese Patent Application (OPI) No. 42045/1983 and British Pat. No. 1,252,418. The advantages of pyrazolotriazole magenta couplers are the absence of any undesired absorption, minimum deterioration of a raw material in the presence of formalin, and high color formability. On the other hand, these couplers are not highly suitable for incorporation in silver halide emulsions because they are so instable in a dispersion that crystal will be easily precipitated. Furthermore, the resulting dye image has a spectral absorption wavelength shorter than the desired value.

When the ballast shown in Japanese Patent Application (OPI) No. 42045/1983 is incorporated in a pyrazolotriazole magenta coupler, the spectral absorption wavelength is shifted to a longer range, but then, high color formability, one great advantage of the pyrazolotriazole magenta coupler, is impaired, and its poor dispersion stability is not at all improved.

SUMMARY OF THE INVENTION

One object of the present invention is to provide a silver halide color photographic material having a silver halide emulsion layer using a highly dispersion-stable magenta coupler.

Another object of the present invention is to provide a silver halide color photographic material that provides a magenta dye image having good spectral absorption characteristics with a spectral absorption wavelength in the range of 550–560 nm and having no undesired absorption in the range of 400–500 nm.

A further object of the present invention is to provide a silver halide color photographic material that provides a magenta dye image having high sensitivity and high color density.

These objects of the present invention can be accomplished by a silver halide color photographic material containing a photographic magenta coupler of formula (I) and a phenolic compound of formula (II) within a silver halide emulsion layer:

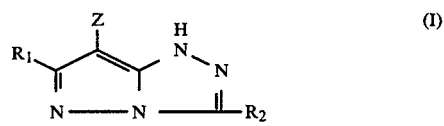

(wherein $R_1$ and $R_2$ are each an alkyl group or an aryl group; Z is a hydrogen atom or a group that can be eliminated upon coupling reaction with the oxidized product of a color developing agent);

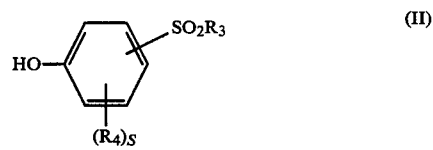

(wherein $R_3$ is an alkyl group, an alkoxy group, an aryl group or an amino group; $R_4$ is an alkyl group, an alkoxy group or a halogen atom; s is an integer of 0 to 2, provided that when s is 2, $R_4$ may be the same or different).

BRIEF DESCRIPTION OF THE DRAWING

FIG. 1 is a diagram showing the absorption spectrum curves of sample Nos. II-1, II-5 and II-6 prepared in Example 2.

DETAILED DESCRIPTION OF THE INVENTION

The alkyl group represented by $R_1$ and $R_2$ in formula (I) is a straight or branched chain having 1 to 8 carbon atoms, and illustrative examples are methyl, methoxymethyl, ethyl, tert-butyl and octyl. These alkyl groups may have a substituent. The aryl group represented by $R_1$ and $R_2$ in formula (I) is preferably a phenyl group. The aryl group may have a substituent. Illustrative substituents on the alkyl group and aryl group include a halogen atom, an alkoxy group, an acylamino group, an aryl group and an alkyl group. Group $R_2$ is preferably an aryl-substituted alkyl group, i.e., aralkyl group, and a ballasted aralkyl group is particularly preferred. Group $R_1$ is preferably an alkyl group, with methyl being particularly preferred.

Group Z in formula (I) which can be eliminated upon coupling reaction with the oxidized product of a color developing agent is illustrated by such specific examples as a halogen atom (e.g. chlorine, bromine, iodine or fluorine), an aryloxy group (e.g. phenoxy, p-methoxyphenoxy, p-butanesulfonamidophenoxy, or p-tert-butylcarboamidophenoxy), an arylthio group (e.g. phenylthio) and a heterocyclic thio group (e.g. 1-ethyltetrazole-5-thioyl). A halogen atom is preferred, and a chlorine atom is particularly preferred. More preferably, the magenta coupler of formula (I) is a two-equivalent magenta coupler of the following formula (IA):

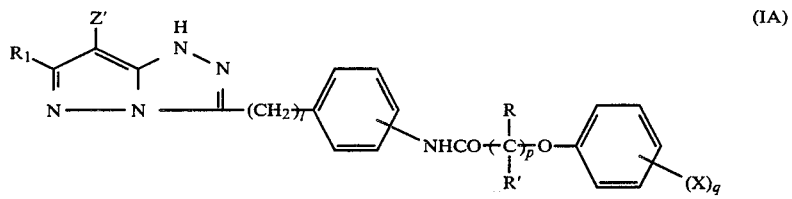

wherein $R_1$ is the same as defined in formula (I); $Z'$ represents a group that can be eliminated upon coupling reaction with the oxidized product of a color developing agent; R and R' are each a hydrogen atom or an alkyl group which is preferably a straight- or branched-chain alkyl group with 1 to 20 carbon atoms, such as methyl, ethyl, n-propyl, iso-propyl, iso-butyl, n-butyl, n-octyl, n-decyl, n-dodecyl or stearyl, provided that R and R' may be the same or different; X is a straight- or branched-chain alkyl group with 1 to 20 carbon atoms (e.g. methyl, ethyl, t-phenyl, t-butyl or n-pentadecyl), a halogen atom (e.g. chlorine, bromine or fluorine), or a hydroxyl group; l, p and q each represents an integer of 0 to 4, on the condition that l preferably represents an integer of from 0 to 3, p from 1 to 3, and q is 1 or 2.

Typical examples of the magenta coupler used in the present invention are listed below, but it should be understood that the scope of the invention is by no means limited to these examples.

[Structure with $R_1$, Z, $R_2$ substituents on pyrazole ring]

| Coupler No. | $R_1$ | Z | $R_2$ |
|---|---|---|---|
| C-1 | $CH_3-$ | $Cl-$ | $-(CH_2)_3-C_6H_4-NHCOCH_2O-C_6H_3(C_5H_{11}(t))_2$ |
| C-2 | $CH_3-$ | $Cl-$ | $-(CH_2)_3-C_6H_4-NHCO(CH_2)_3O-C_6H_3(C_5H_{11}(t))_2$ |
| C-3 | $CH_3-$ | $Cl-$ | $-CH_2-C_6H_4(NHCOCH_2-O-C_6H_4-C_{15}H_{31})$ |
| C-4 | $CH_3-$ | $Cl-$ | $-(CH_2)_2-C_6H_4-NHCO(CH_2)_3O-C_6H_4-C_{15}H_{31}$ |
| C-5 | $CH_3-$ | $Cl-$ | $-(CH_2)_2-C_6H_3(Cl)-NHCOCH(C_2H_5)-O-C_6H_4-C_{15}H_{31}$ |

-continued

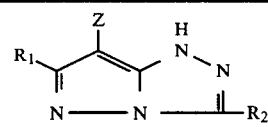

| Coupler No. | $R_1$ | Z | $R_2$ |
|---|---|---|---|
| C-6 | $(CH_3)_3C-$ | Cl | $-(CH_2)_3-C_6H_4-NHCOCH(C_2H_5)O-C_6H_3(C_5H_{11}(t))_2$ |
| C-7 | $CH_3-$ | Cl— | $-(CH_2)_3-C_6H_4-NHCOCH(C_{12}H_{25})O-C_6H_3(OH)(C_4H_9(t))$ |
| C-8 | $CH_3O-C_6H_4-$ | Cl— | $-(CH_2)_3-C_6H_4-NHCOCH(C_{10}H_{21})O-C_6H_3(C_4H_9(t))(OH)$ |
| C-9 | $CH_3-$ | $CH_3O-C_6H_4-$ | $-(CH_2)_3-C_6H_4-NHCOCH(C_4H_9)O-C_6H_3(C_5H_{11}(t))_2$ |
| C-10 | $CH_3-$ | Cl— | $(CH_2)_3-C_6H_4-NHCOCH(CH(CH_3)_2)O-C_6H_3(C_5H_{11}(t))_2$ |
| C-11 | $C_6H_5-$ | Cl— | $-(CH_2)_2-C_6H_4-NHCOCH_2O-C_6H_4-OC_{18}H_{35}$ |
| C-12 | $(CH_3)_3C-$ | Cl— | $-(CH_2)_2-C_6H_4-NHCOCH(C_2H_{25})O-C_6H_3(C_5H_{11}(t))_2$ |
| C-13 | $CH_3-$ | Cl— | $-(CH_2)_2-C_6H_4-NHSO_2-C_6H_4-OC_{18}H_{37}$ |
| C-14 | $CH_3-$ | Cl— | $-(CH_2)_2-C_6H_4-NHCOCH(C_{10}H_{21})O-C_6H_4-SO_2-C_6H_4-OH$ |
| C-15 | $CH_3-$ | H— | $-C_6H_4-NHCOCH(C_2H_5)O-C_6H_3(C_5H_{11}(t))_2$ |
| C-16 | $(CH_3)_3C-$ | H— | $-C_{18}H_{37}$ |

| Coupler No. | $R_1$ | Z | $R_2$ |
|---|---|---|---|
| C-17 | $CH_3-$ | $Cl-$ | 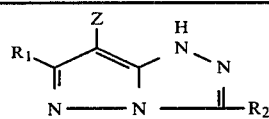 |
| C-18 | $CH_3-$ | $Cl-$ | $\text{-(CH}_2\text{)}_3\text{-C}_6\text{H}_4\text{-NHCOCH(C}_{12}\text{H}_{25}\text{)SO}_2\text{CH}_2\text{-C}_6\text{H}_5$ |

The alkyl group represented by $R_3$ in formula (II) is a straight- or branched-chain alkyl group with 1 to 20 carbon atoms (e.g. methyl, ethyl, tert-butyl, tert-amyl, tert-octyl, n-nonyl or n-dodecyl), and the alkoxy group represented by $R_3$ is a straight- or branched-chain alkoxy group with 1 to 20 carbon atoms (e.g. methoxy, ethoxy, tert-butoxy, n-octyloxy or n-dodecyloxy). The aryl group represented by $R_3$ is typically a phenyl or naphthyl group. The alkyl, alkoxy and aryl groups each represented by $R_3$ may have a substituent. Suitable substituents include a halogen atom (e.g., chlorine, bromine or fluorine), and commonly known monovalent organic groups such as a straight- or branched-chain alkyl group having 1 to 20 carbon atoms (e.g., methyl, ethyl, iso-propyl, t-pentyl, dodecyl or stearyl), a straight- or branched-chain alkoxy group having 1 to 20 carbon atoms (e.g., methoxy, ethoxy, iso-propoxy, dodecyloxy or stearyloxy), a straight- or branched-chain acylamino group with 1 to 20 carbon atoms (e.g., acetamido, butaneamido or octadecaneamido), a straight- or branched-chain alkylsulfonamido group having 1 to 20 carbon atoms wherein the alkyl moiety is the same as defined for $R_3$, and a substituted or unsubstituted arylsulfonamido group wherein the aryl moiety is the same as defined for $R_3$. These substituents may be further substituted by commonly known organic groups. The amino group represented by $R_3$ may be substituted by an alkyl or phenyl group.

The alkyl group and alkoxy group represented by $R_4$ in formula (II) are the same as defined by $R_3$. Examples of the halogen atom include chlorine, bromine and fluorine atoms.

Preferred phenolic derivative of formula (II) is such that s is 0 and group $-SO_2R_3$ is bonded to phenol at para-position with respect to the hydroxyl group. A more preferred phenolic derivative is such that $R_3$ in the group $-SO_2R_3$ is a phenyl group, with a substituted phenyl group being particularly preferred as $R_3$. A particularly preferred substituent is an alkoxy group.

Typical examples of the phenolic compound used in the present invention are given below, but it should be understood that the scope of the invention is by no means limited to these examples.

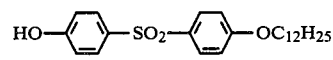 P-1

$HO-C_6H_4-SO_2-C_6H_4-OCH_2CH(C_2H_5)C_4H_9$  P-2

$HO-C_6H_4-SO_2-C_6H_4-OC_8H_{16}CH=CH-C_8H_{17}$  P-3

$HO-C_6H_4-SO_2-C_6H_4-OC_{18}H_{37}$  P-4

$HO-C_6H_4-SO_2-C_6H_4-OC_4H_9(t)$  P-5

$HO-C_6H_4-SO_2-C_6H_4-OCH_3$  P-6

$HO-C_6H_4-SO_2-C_6H_4-OC_4H_9(n)$  P-7

$HO-C_6H_4-SO_2-C_6H_4-OC_8H_{17}$  P-8

$HO-C_6H_4-SO_2-C_6H_4-OC_{14}H_{29}$  P-9

$HO-C_6H_4-SO_2-C_6H_4-OC_{16}H_{33}$  P-10

$HO-C_6H_4-SO_2-C_6H_4-OC_9H_{18}CH=CH_2$  P-11

$HO-C_6H_4-SO_2-C_6H_4-O-C_6H_{11}$  P-12

$HO-C_6H_4-SO_2-C_6H_4-OCH_2CH_2-C_6H_4-NHCOC_{11}H_{23}$  P-13

$HO-C_6H_4-SO_2-C_6H_4-OCH_2CONHC_{14}H_{29}$  P-14

$HO-C_6H_4-SO_2-C_6H_4-OCH(C_{12}H_{25})COOC_2H_5$  P-15

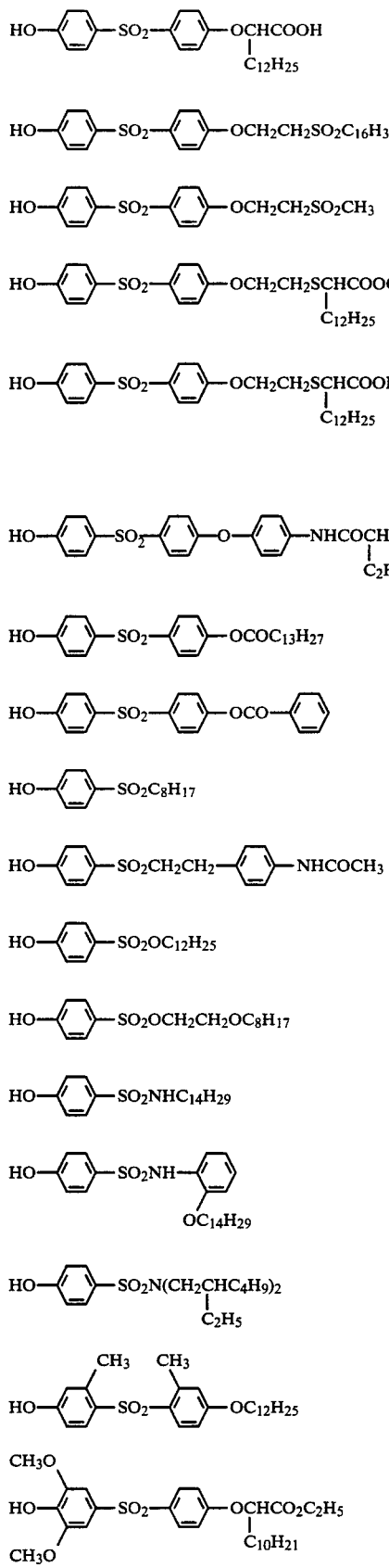

The synthesis of two magenta couplers used in the present invention is shown below.

Synthesis 1: Coupler C-2

To a solution of anhydrous sodium acetate (4.5 g) in acetic acid (150 cc), 6-methyl-3-[3-(p-aminophenyl)-propyl]-1H-pyrazole (3,2-c)-s-triazole (12.7 g) was added at room temperature, and under agitation, γ-(2,4-di-tert-amylphenoxy)butanoyl chloride (18.6 g) was added in small portions. Following 8-hr agitation, the reaction mixture was poured into water. An oily product formed. It was extracted with ethyl acetate and washed with water. The oily layer was separated and dried with anhydrous magnesium sulfate. After distilling off the solvent under vacuum, the residue was purified by column chromatography on silica gel, and crystallized with ethyl acetate and n-hexane to give a white powder (15.3 g).

Part (11.1 g) of the white powder was uniformly dissolved in chloroform (110 cc), and under cooling with iced water at 10° C.±5° C., a solution of sulfuryl chloride (3.0 g) in chloroform (30 cc) was slowly added dropwise over a period of 1 hr. Following reaction for another one hour at the same temperature, the reaction mixture was poured into water for washing and separating the chloroform layer. It was dried with anhydrous magnesium sulfate and the solvent was distilled off under vacuum. The residue was purified by column chromatography on silica gel and recrystallized with acetonitrile.

A white powder (4.8 g) having mp. 148°–149° C. formed, and its structure was determined by NMR and MASS analyses.

Synthesis 2: Coupler C-7

To a solution of anhydrous sodium acetate (4.5 g) in acetic acid (150 cc), 6-methyl-3-[3-(p-aminophenyl)-propyl]-1H-pyrazole (3,2-c)-s-triazole (12.7 g) was added at room temperature, and under agitation, α-(4-acetyloxy-3-tertbutylphenoxy)tetradecanoyl chloride (25.0 g) was added in small portions. Following 6-hr agitation, the reaction mixture was poured into water. An oily product formed. It was extracted with ethyl acetate and washed with water. The oily layer was separated and dried with anhydrous magnesium sulfate. After distilling off the solvent under vacuum, the residue was purified by column chromatography on silica gel to give a white oil (24.5 g).

Part (20 g) of the white oil was dissolved in chloroform (200 cc), and under cooling with iced water at 10° C.±3° C., a solution of sulfuryl chloride (4.5 g) in chloroform (45 cc) was added dropwise over a period of one hour. Following reaction for another one hour at the same temperature, water was added for washing and separating the chloroform layer. It was dried with anhydrous magnesium sulfate and the solvent was distilled off. The residue was subjected to column chromatography on silica gel to obtain a white oil (8.5 g).

Part (7.1 g) of the white oil was poured into a solution of sodium hydroxide (1.2 g) in a mixture of ethanol (30 cc) and water (30 cc), and the mixture was heated at 40° C.±5° C. for one hour. The reaction mixture was rendered acidic with HCl. An oily product formed. It was extracted with ethyl acetate and washed with water. The oily layer was separated and dried with anhydrous magnesium sulfate. After distilling off the solvent under vacuum, the residue was purified by column chromatography on silica gel and recrystallized from acetonitrile.

A white powder (3.6 g) having mp. 63°–65° C. was obtained and its structure was determined by NMR and MASS analyses.

The phenolic compound of the present invention can be readily synthesized by any of the known methods. A typical method is shown below.

Synthesis 3: Compound P-1

To an aqueous solution (400 cc) of bisphenol S (50 g and anhydrous potassium carbonate (30 g), dodecyl bromide (50 g) was gradually added dropwise at 70° C. under agitation. Following 2-hour reaction, the liquid mixture was cooled, extracted with ether and washed thoroughly with aqueous 1 N $K_2CO_3$. The ether layer was washed with water and dried. After distilling off the solvent, the residue was mixed with hexane for crystallization. By filtration, 40 g of a white crystal (mp. 57°–58° C.) was obtained.

Other phenolic compounds suitable for use in the present invention may be synthesized by a similar method. The magenta coupler according to the present invention is used in a manner similar to that used with conventional magenta dye forming couplers. Typically, the magenta coupler of the present invention is incorporated in a silver halide emulsion, which is then applied to a base to form a silver halide color photographic material. The silver halide photographic material may be monochromatic or multi-colored. In the latter case, the magenta coupler of the present invention is usually incorporated in a green-sensitive emulsion, but if desired, the coupler may be incorporated in an unsensitized emulsion layer or an emulsion layer which is sensitive to the primary color regions in the spectrum other than green.

Each of the units that are used in the silver halide color photographic material of the present invention for providing dye images is made of one or more emulsion layers having sensitivity to specified ranges in the spectrum.

The layers necessary for making the silver halide color photographic material including the image forming layers may be arranged in various orders known in the art. A typical multi-colored silver halide photographic material consists of a cyan dye image forming unit comprising at least one red-sensitive silver halide emulsion layer containing at least one cyan dye forming coupler, a magenta dye image forming unit comprising at least one green-sensitive silver halide emulsion layer containing at least one magenta dye forming coupler as defined in the present invention, and a yellow dye image forming unit comprising at least one blue-sensitive silver halide emulsion layer containing at least one yellow dye forming coupler, with these three image forming units carried on a support.

The photographic material according to the present invention may contain additional layers such as a filter layer, an intermediate layer, a protective layer and a subbing layer.

The magenta coupler and the phenolic compound according to the present invention may be incorporated in a silver halide photographic material by any of the known methods. For example, the magenta coupler and the forming phenolic compound according to the present invention are dissolved, either independently or in combination, in a mixture of a known high-boiling solvent and a low-boiling solvent such as butyl acetate or butyl propionate; the solution is then mixed with an aqueous solution of gelatin containing a surfactant; the mixture is emulsified with a high-speed rotary mixer, colloid mill or an ultrasonic disperser, and the resulting emulsion is added to a separately prepared silver halide, thereby forming a desired silver halide emulsion for use in the present invention.

Typical known high-boiling solvents include phthalic esters (e.g., dibutyl phthalate and dioctyl phthalate), phosphate esters (e.g., tricresyl phosphate and trioctyl phosphate) and N-substituted acid amides (e.g., N,N-diethyllaurylamide).

The phenolic compound of the present invention may be dispersed separately from the magenta coupler of the present invention, and the two are individually added to the same silver halide emulsion. Preferably, the two are dissolved and added in the silver halide emulsion simultaneously.

For incorporation in the silver halide emulsion, the magenta coupler according to the present invention is used in an amount which generally ranges from about 0.01 to 2 mols, preferably from 0.03 to 0.5 mol, per mol of silver halide.

The greater the amount of the phenolic compound of the present invention that is used in comparison with the magenta coupler of the present invention, the more favorable it is to the objects of the present invention. Stated more specifically, the phenolic compound of the present invention is used in an amount of 0.1 to 10 g, preferably 0.25 to 3 g, per gram of the magenta coupler of the present invention.

The silver halide used in the silver halide emulsion according to the present invention is selected from among any of those which are used in conventional silver halide emulsions, such as silver bromide, silver chloride, silver iodobromide, silver chlorobromide and silver chloroiodobromide.

The silver halide emulsions making up the silver halide emulsion layers according to the present invention may be prepared by any of the common techniques. A typical example is shown in Japanese Patent Publication No. 7772/1971 and concerns the production of a "conversion emulsion": an emulsion of silver salt particles at least part of which has a higher solubility than silver bromide is first prepared, and then, at least part of these grains is converted to silver bromide or silver iodobromide. Alternatively, the method for preparing a Lippmann emulsion composed of fine silver halide grains having an average size of 0.1 µm or less may be employed.

The silver halide emulsions according to the present invention may be chemically sensitized by a sulfur sensitizer e.g., arylthiocarbamide, thiourea or cystine), an active or inactive selenium sensitizer, a reduction sensitizer (e.g. stannous salt or polyamine), a noble metal sensitizer such as a gold sensitizer (e.g. potassium aurithiocyanate, potassium chloroaurate or 2-aurosulfobenzothiazole methyl chloride) or a water-soluble salt of ruthenium, rhodium or iridium (e.g. ammonium chloropalladate, potassium chloroplatinate or sodium chloropalladite). These chemical sensitizers may be used either alone or in combination.

The silver halide emulsions used in the present invention may contain various known photographic additives, such as those shown in Research Disclosure, December 1978, No. 17643.

The silver halide used in the present invention may be spectrally sensitized with a suitable sensitizing dye for the purpose of affording sensitivity to the necessary wavelength range. Various spectral sensitizers may be employed either alone or in combination. Those which are used with advantage in the present invention are cyanine dyes, merocyanine dyes or complex cyanine dyes of the types shown in U.S. Pat. Nos. 2,269,234, 2,270,378, 2,442,710, 2,454,520 and 2,776,280.

The support used in the present invention may be properly selected from among known materials depending upon the specific type of the photographic material used, and suitable support materials are plastic films, plastic laminated paper, baryta paper, and synthetic paper. These supports are generally subbed to provide a stronger adhesion to a photographic emulsion layer.

The silver halide color photographic material of the present invention shown above is exposed and subjected to various methods of color development. A color developer preferably used in processing the photographic material of the present invention contains an aromatic primary amine color developing agent as the main component. Typical color developing agents are p-phenylenediamine compounds, such as diethyl-p-phenylenediamine hydrochloride, monomethyl-p-phenylenediamine hydrochloride, dimethyl-p-phenylenediaminehydrochloride, 2-amino-5-diethylaminotoluene hydrochloride, 2-amino-5-(N-ethyl-N-dodecylamino)-toluene, 2-amino-5-(N-ethyl-N-$\beta$-methanesulfonamidoethyl)aminotoluene sulfate, 4-(N-ethyl-N-$\beta$-methanesulfonamidoethylamino)aniline, 4-(N-ethyl-N-$\beta$-hydroxyethylamino)aniline, and 2-amino-5-(N-ethyl-$\beta$-methoxyethyl)aminotoluene. These color developing agents may be used either alone or in combination with themselves. They may also be used with black-and-white developing agents such as hydroquinone. The color developing solutions used in the present invention generally contain an alkali agent such as sodium hydroxide, ammonium hydroxide, sodium carbonate or sodium sulfite, as well as other additives such as an alkali metal halide (e.g., potassium bromide) and a development regulator (e.g., hydrazine acid).

The silver halide color photographic material of the present invention may contain the color developing agent in a hydrophilic colloidal layer in the form of its precursor. A precursor of the color developing agent is a compound that is capable of producing the developing agent under alkaline conditions. Illustrative precursors are Schiff base precursors with aromatic aldehyde derivatives, polyvalent metallic ion complex precursors, phthalimide derivative precursors, phosphamide derivative precursors, sugar-amine reaction product precursors, and urethane precursors. Illustrative precursors for the aromatic primary color developing agent are shown in U.S. Pat. Nos. 3,342,599, 2,507,114, 2,695,234, 3,719,492, British Pat. No. 803,783, Japanese Patent Application (OPI) Nos. 135628/1978, 79035/1979, Research Disclosure Nos. 15,159, 12,146 and 13,924.

The aromatic primary amine color developing agents or their precursors shown above must be present in amounts sufficient to provide the desired color as a result of color development. The necessary amount varies significantly depending upon the type of the photographic material to be processed, and generally, it ranges from 0.1 mol to 5 mols, preferably from 0.5 mol to 3 mols, per mol of light-sensitive silver halide. The color developing agents or their precursors may be used either alone or in combination. These compounds may be incorporated in the photographic material either by dissolving them in a suitable solvent such as water, methanol, ethanol or acetone, or by using an emulsion in a high-boiling solvent such as dibutyl phthalate, dioctyl phthalate or tricresyl phosphate. If desired, the compounds may be impregnated in a latex polymer as shown in Research Disclosure No. 14850.

After color development, the silver halide color photographic material of the present invention is bleached, fixed and washed with water. The steps of bleaching and fixing may be performed simultaneously as a bleach-fixing step. While may compounds may be used is bleaching agents, compounds of polyvalent metals such as iron (III), cobalt (III) and tin (II) are preferably used. Particularly preferred compounds are complex salts of these polyvalent metallic cations and organic acids such as aminopolycarboxylic acids (e.g., ethylenediaminetetraacetic acid, nitrilotriacetic acid, and N-hydroxyethylenediaminediacetic acid), or organic acids (e.g., malonic acid, tartatic acid, malic acid diglycolic acid and dithioglycolic acid). Alternatively, ferricyanates and bichromates may be used. These bleaching compounds may be used either alone or in combination.

By using the magenta coupler and phenolic compound in combination as shown above, the silver halide color photographic material of the present invention provides a dye image having a maximum spectral absorption in a sufficiently longer wavelength region. Furthermore, the magenta dye formed by the photographic material of the present invention does not have any absorption in the spectrum of 400–500 nm that is not desired, and therefore, an image of good color reproduction can be obtained. As other advantages, the photographic material of the present invention has high sensitivity and exhibits high color forming ability (i.e., high color density).

SPECIFIC EMBODIMENTS OF THE INVENTION

The present invention is hereunder described in greater detail by reference to working examples, to which the possible embodiments of the present invention are by no means limited.

EXAMPLE 1

The magenta couplers shown in Table 1 were each used in an amount of 6 g. The phenolic compounds also shown in Table 1 were each used in an amount of 3 g. To the magenta couplers, some of which were combined with phenolic compounds and some were not, 4 g of tricresyl phosphate and 18 g of ethyl acetate were added. The mixture was heated at 60° C. to obtain a complete solution. The solution was mixed with 150 ml of a 5% aqueous gelatin solution containing 15 ml of a 5% aqueous solution of Alkanol B (alkyl naphthalenesulfonate, a product of E. I. du Pont de Nemours & Co.), and an emulsion was prepared from the mixture by treatment with an ultrasonic disperser. This emulsion was subjected to vacuum distillation to remove ethyl acetate.

A green-sensitive silver iodobromide emulsion (500 g) was centrifuged to remove any silver halide grains. The residue was mixed with the previously prepared emulsion and the mixture was held at 60° C. on a water bath for examining the stability of each coupler in dispersion by measuring the time necessary for the coupler to start crystalizing under an optical microscope (X 600). The results are shown in Table 1.

Table 1

| Sample No. | Coupler | Phenolic compound | Time to crystallize (hr) |
|---|---|---|---|
| I - 1 | C - 2 | none | 2 |
| I - 2*(1) | C - 2 | none | 4 |
| I - 3 | C - 2 | P - 1 | 10 |
| I - 4 | C - 2 | P - 3 | 8 |
| I - 5 | C - 2 | P - 15 | ≧12 |
| I - 6 | C - 2 | P - 28 | 10 |
| I - 7 | C - 7 | none | 3 |
| I - 8 | C - 7 | P - 1 | ≧12 |
| I - 9 | C - 7 | P - 17 | ≧12 |
| I - 10 | C - 7 | P - 27 | 10 |
| I - 11 | C - 14 | none | 2 |
| I - 12 | C - 14 | P - 15 | 10 |
| I - 13 | C - 14 | P - 21 | 8 |
| I - 14 | C - 14 | P - 24 | 8 |

*(1)Three more grams of tricresyl phosphate was used.

As Table 1 shows, the magenta couplers of the present invention crystallized very rapidly when they were independently dispersed in high-boiling organic solvents. This defect was not eliminated even when a larger amount of high-boiling organic solvent was used (Sample I-2). Good results were obtained when the magenta couplers of the present invention were dispersed in high-boiling organic solvents together with the phenolic compounds of the present invention because a much longer time was necessary before the couplers started to crystalize.

EXAMPLE 2

The magenta couplers shown in Table 2 (four of which were samples of the present invention and the other three were comparative samples) were used each in an amount of 0.1 mole per mole of silver. For several samples, the phenolic compounds also shown in Table 2 were used each in a molar equivalent amount with respect to the coupler. Also used were tricresyl phosphate (the same as the weight of the coupler) and ethyl acetate (three times the weight of the coupler). The mixture of the four components (if no phenolic compound was used, the components were three) was heated at 60° C. to make a complete solution.

The solution was mixed with 600 ml of a 5% aqueous gelatin solution containing 120 ml of a 5% aqueous solution of Alkanol B (alkyl naphthalenesulfonate, a product of E. I. Du Pont de Nemours & Co.), and an emulsion was prepared from the mixture by treatment with an ultrasonic disperser. The dispersion was mixed with 2.4 kg of a green-sensitive silver iodobromide emulsion (containing 6 mol % of silver iodide) in the presence of 90 ml of a hardener, or 2% solution of 1,2-bis(vinylsulfonyl)ethane in water/methanol (1:1). The mixture was applied to a subbed transparent polyester base and the web was dried.

By this procedure, samples II-1 to II-19 of silver halide photographic material were prepared. In all samples, the silver deposit was 20 mg/100 cm$^2$.

The samples thus prepared were exposed to light through a wedge by the conventional method and processed according to the following acheme. The results are shown in Table 2.

| Processing (38° C.) | Time |
|---|---|
| Color development | 3 min 15 sec |
| Bleaching | 1 min 30 sec |
| Washing | 3 min 15 sec |
| Fixing | 6 min 30 sec |
| Washing | 3 min 15 sec |
| Stabilizing | 1 min 30 sec |

The solutions used in the respective processing steps had the following formulation.

| Components | Amount (g) |
|---|---|
| Color developer | |
| 4-Amino-3-methyl-N-ethyl-N-(β-hydroxyethyl)-aniline sulfate | 4.75 |
| Anhydrous sodium sulfite | 4.25 |
| Hydroxylamine hemisulfate | 2.0 |
| Anhydrous potassium carbonate | 37.5 |
| Sodium bromide | 1.3 |
| Nitrilotriacetic acid trisodium salt (monohydrate) | 2.1 |
| Potassium hydroxide | 1.0 |
| Water to make | 1,000 ml |
| pH adjusted to 10.0 with KOH | |
| Bleaching solution | |
| Ethylenediaminetetraacetic acid iron ammonium salt | 100.0 g |
| Ethylenediaminetetraacetic acid diammonium salt | 10.0 g |
| Ammonium bromide | 150.0 g |
| Glacial acetic acid | 10.0 ml |
| Water to make | 1,000 ml |
| pH adjusted to 6.0 with ammonia water | |
| Fixing solution | |
| Ammonium thiosulfate (50% aq. sol.) | 162 ml |
| Anhydrous sodium sulfite | 12.4 ml |
| Water to make | 1,000 ml |
| pH adjusted to 6.5 with acetic acid | |
| Stabilizing bath | |
| Formalin (37% aq. sol.) | 5.0 ml |
| Konidax (product of Konishiroku Photo Industry Co., Ltd.) | 7.5 ml |
| Water to make | 1,000 ml |

TABLE 2

| Sample No. | Coupler | Phenolic compound | Sensitivity*(1) | Maximum density | Maximum absorption (nm) |
|---|---|---|---|---|---|
| II-1 | Comparative coupler 1 | none | 100 | 2.00 | 554 |
| II-2 | Comparative coupler 2 | none | 230 | 2.88 | 551 |
| II-3 | Comparative coupler 3 | none | 150 | 3.37 | 543 |
| II-4 | C-2 | none | 247 | 3.40 | 546 |
| II-5*(2) | C-2 | none | 195 | 3.00 | 544 |
| II-6 | C-2 | P-1 | 302 | 3.95 | 551 |
| II-7 | C-2 | P-15 | 310 | 4.02 | 551 |
| II-8 | C-2 | P-24 | 280 | 3.88 | 549 |
| II-9 | C-2 | P-28 | 290 | 3.90 | 550 |
| II-10 | C-7 | none | 206 | 3.88 | 549 |
| II-11 | C-7 | P-3 | 232 | 4.2 | 552 |
| II-12 | C-7 | P-15 | 252 | 4.4 | 553 |
| II-13 | C-7 | P-30 | 225 | 4.1 | 552 |
| II-14 | C-14 | none | 110 | 3.42 | 552 |
| II-15 | C-14 | P-1 | 150 | 3.90 | 554 |
| II-16 | C-14 | P-5 | 140 | 3.82 | 553 |
| II-17 | C-13 | none | 198 | 3.25 | 547 |
| II-18 | C-13 | P-19 | 285 | 3.75 | 551 |

TABLE 2-continued

| Sample No. | Coupler | Phenolic compound | Sensitivity*[1] | Maximum density | Maximum absorption (nm) |
|---|---|---|---|---|---|
| II-19 | C-13 | P-34 | 291 | 3.88 | 550 |

*[1] The sensitivity is the reciprocal of exposure that gave a density equal to fog + 0.1. The data on sensitivity is based on relative values, with the value for comparative coupler 1 being taken as 100.

*[2] Twice the amount of coupler of tricresyl phosphate was used.

Comparative Coupler 1:

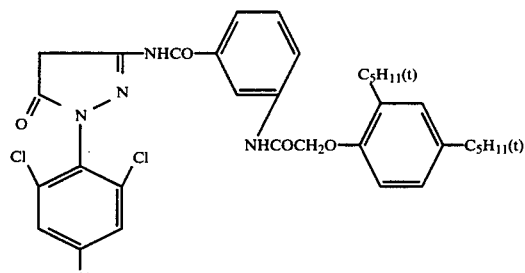

Comparative Coupler 2 (as shown in Japanese Patent Publication No. 16058/1974):

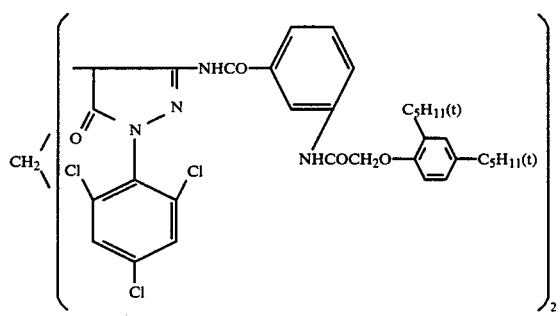

Comparative Coupler 3 (as shown in U.S. Pat. No. 3,684,514):

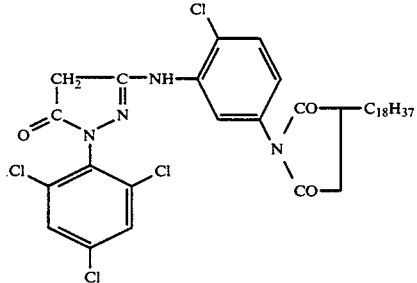

As Table 2 shows, Comparative coupler 1 had a sufficiently high maximum absorption but it was poor in both sensitivity and maximum density. Comparative coupler 2 was satisfactory in maximum absorption and sensitivity but had low maximum density. Comparative coupler 3 was satisfactory in both sensitivity and maximum density but its maximum absorption was on the shorter wavelength side and did not achieve the object of the present invention. Comparative Coupler 1 had a further disadvantage in that it had an undesired absorption at about 430 nm (see FIG. 1).

The magenta couplers according to the present invention used independently were satisfactory in both sensitivity and maximum density, but they had maximum absorptions on the shorter wavelength side and did not achieve the object of the present invention. When the magenta couplers were dissolved in an increased amount of high-boiling organic solvent, not only did their sensitivity and color density drop but also their maximum absorption shifted to the shorter wavelength side, which was not good for the purpose of the present invention.

These problems were solved when the magenta couplers of the present invention were used in combination with the phenolic compounds of the present invention. Sufficient sensitivity and maximum density were achieved, and maximum absorption peaks occurring on the longer wavelength side that fitted the purpose of the present invention were obtained. Therefore, data in Tables 1 and 2 reveal that the object and advantages of the present invention can be accomplished only when the magenta coupler of the present invention is used in combination with the phenolic compound of the present invention. This combined use provides an appreciably improved result both in color sensitivity and in maximum density.

These observations are visualized in FIG. 1 which show the absorption spectra (wavelength vs. density) of sample II-1 (outside the scope of the present invention), sample II-5 (also outside the scope of the present invention) and sample II-6 (according to the present invention) which were prepared in Example 2. In FIG. 1, the three samples are indicated by one-long-and-one-short dashed line, dashed line and solid line, respectively.

As is clear from FIG. 1, sample II-1 containing comparative coupler 1 had a maximum absorption on the longer wavelength side but had an undesired absorption peak at about 430 nm. Sample II-5 containing coupler C-2 of the present invention without using the phenolic compound of the present invention did not have any undesired absorption peak at 430 nm, but its maximum absorption peak occurred on the shorter wavelength side and failed to achieve the purpose of the present invention. Sample II-6 using the magenta coupler and phenolic compound of the present invention in combination had no unwanted absorption peak and exhibited a maximum absorption on the desired longer wavelength side.

What is claimed is:

1. A silver halide color photographic material containing a photographic magenta coupler of formula (I) and a phenolic compound of formula (II) within a silver halide emulsion layer:

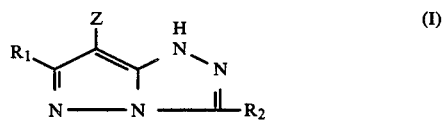

(wherein $R_1$ and $R_2$ are each an alkyl group or an aryl group; Z is a hydrogen atom or a group that can be eliminated upon coupling reaction with the oxidized product of a color developing agent);

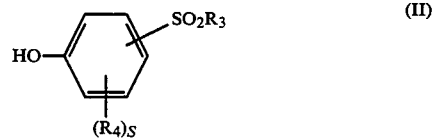

(wherein $R_3$ is an alkyl group, an alkoxy group, an aryl group or an amino group; $R_4$ is an alkyl group, an alkoxy group or a halogen atom; s is an integer of 0 to 2, provided that when s is 2, $R_4$ may be the same or different).

2. A silver halide color photographic material according to claim 1 wherein the alkyl group represented by $R_1$ and $R_2$ in formula (I) has 1 to 8 carbon atoms.

3. A silver halide color photographic material according to claim 1 wherein the aryl group represented by $R_1$ and $R_2$ in formula (I) is a phenyl group.

4. A silver halide color photographic material according to claim 1 wherein $R_2$ in formula (I) is an aryl-substituted alkyl group.

5. A silver halide color photographic material according to claim 1 wherein Z in formula (I) is selected from the group consisting of a halogen atom, an aryloxy group, an arylthio group, and a heterocyclic thio group.

6. A silver halide color photographic material according to claim 1 wherein the magenta coupler has the following formula (IA):

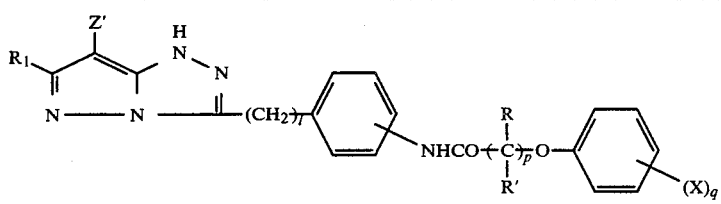

(IA)

wherein $R_1$ is the same as defined for formula (I); $Z'$ is a group that can be eliminated upon coupling with the oxidized product of a color developing agent; R and R' are each a hydrogen atom or an alkyl group; X is a straight- or branched-chain alkyl group having 1 to 20 carbon atoms, a halogen atom or a hydroxyl group; l, p and q are each an integer of 0 to 4.

7. A silver halide color photographic material according to claim 6 wherein $R_1$ in formula (IA) is an alkyl group having 1 to 8 carbon atoms.

8. A silver halide color photographic material according to claim 6 wherein $Z'$ in formula (IA) is selected from the group consisting of a halogen atom, an aryloxy group, an arylthio group and a heterocyclic thio group.

9. A silver halide color photographic material according to claim 6 wherein the alkyl group represented by R and R' in formula (IA) is a straight- or branched-chain alkyl group having 1 to 20 carbon atoms.

10. A silver halide color photographic material according to claim 6 wherein l in formula (IA) is an integer of 0 to 3, p is an integer of 1 to 3, and q is 1 or 2.

11. A silver halide color photographic material according to claim 1 wherein the alkyl group represented by $R_3$ in formula (II) is a straight- or branched-chain alkyl group having 1 to 20 carbon atoms.

12. A silver halide color photographic material according to claim 1 wherein the alkoxy group represented by $R_3$ in formula (II) is a straight- or branched-chain alkoxy group having 1 to 20 carbon atoms.

13. A silver halide color photographic material according to claim 1 wherein the alkyl group represented by $R_4$ in formula (II) is a straight- or branched-chain alkyl group having 1 to 20 carbon atoms.

14. A silver halide color photographic material according to claim 1 wherein the alkoxy group represented by $R_4$ in formula (II) is a straight- or branched-chain alkoxy group having 1 to 20 carbon atoms.

15. A silver halide color photographic material according to claim 1 wherein s in formula (II) is zero.

16. A silver halide color photographic material according to claim 1 wherein the group $SO_2R_3$ in formula (II) is attached to the phenyl group at a para-position with respect to the hydroxy group.

* * * * *